(12) United States Patent
Dai et al.

(10) Patent No.: US 12,213,910 B1
(45) Date of Patent: Feb. 4, 2025

(54) COLD THERAPY SYSTEM AND COLD THERAPY DEVICE

(71) Applicant: JKH USA, LLC, Lake Forest, CA (US)

(72) Inventors: Quanqin Dai, Lake Forest, CA (US); Pu Jiang, Shenzhen (CN)

(73) Assignee: JKH USA, LLC, Lake Forest, CA (US)

( * ) Notice: Subject to any disclaimer, the term of this patent is extended or adjusted under 35 U.S.C. 154(b) by 0 days.

(21) Appl. No.: 18/661,568

(22) Filed: May 10, 2024

(30) Foreign Application Priority Data

Dec. 6, 2023 (CN) .......................... 202323335220.3
Feb. 4, 2024 (CN) .......................... 202420272993.7

(51) Int. Cl.
*A61F 7/00* (2006.01)

(52) U.S. Cl.
CPC .... *A61F 7/0085* (2013.01); *A61F 2007/0056* (2013.01); *A61F 2007/0092* (2013.01)

(58) Field of Classification Search
CPC ................. A61F 2007/0054; A61F 2007/0056
See application file for complete search history.

(56) References Cited

U.S. PATENT DOCUMENTS

| | | | | |
|---|---|---|---|---|
| 5,226,553 | A * | 7/1993 | Fiore | A45C 11/20 220/765 |
| 6,551,348 | B1 * | 4/2003 | Blalock | A61F 7/0085 607/104 |
| 7,640,764 | B2 * | 1/2010 | Gammons | F25D 3/08 607/104 |
| 9,877,864 | B2 * | 1/2018 | Parish | A61F 7/00 |
| 2004/0068309 | A1 * | 4/2004 | Edelman | A61F 7/02 607/104 |

* cited by examiner

*Primary Examiner* — Kaitlyn E Smith
(74) *Attorney, Agent, or Firm* — Arch & Lake LLP

(57) ABSTRACT

The present disclosure provides cold therapy system and device. The cold therapy system includes a bucket body and a bucket lid, the bucket lid includes: a first water circuit configured to input the cold therapy liquid from the bucket body to a cold therapy pad; a second water circuit configured to output the cold therapy liquid from the cold therapy pad to the bucket body; and a water pump configured to drive the cold therapy liquid to flow in a loop including the first water circuit, the second water circuit and the bucket body; wherein the first water circuit includes: a pumping orifice, a first guide tube, a second guide tube; and wherein the second water circuit includes: at least one return orifice, a third guide tube. The return orifice with an opening facing in the direction of the bucket body, provided at a predetermined distance from the pumping orifice.

18 Claims, 8 Drawing Sheets

COLD THERAPY SYSTEM AND COLD THERAPY DEVICE

CROSS REFERENCE TO RELATED APPLICATIONS

This present application claims the benefit of priority to Chinese Patent Application No. 202420272993.7, filed on Feb. 4, 2024, and Chinese Patent Application No. 202323335220.3, filed on Dec. 6, 2023, the disclosures of which are incorporated herein by reference in their entireties for all purposes.

TECHNICAL FIELD

The present disclosure relates to the field of medical devices, and in particular, relates to a cold therapy system and a cold therapy device.

BACKGROUND

Cold therapy is often used in nursing because it causes vasoconstriction of the blood vessels at the site of skin contact, which reduces local swelling, reduces nerve sensitivity and provides pain relief. In addition, the number of people participating in sports activities has increased significantly in recent years, and cold therapy is often needed to relieve fatigue after exercise.

The demand for cold therapy has led to a demand for cold therapy equipment, especially simple and convenient cold therapy equipment that can be used at home or elsewhere.

Existing cold therapies typically use cold therapy pads, which are filled with cold therapy fluid and then placed against or wrapped around the part of the body to be treated. However, after the cold therapy liquid enters the cold therapy pad, the heat exchange with the human body, the temperature of the cold therapy liquid will rise, the high temperature cold therapy liquid returned to the bucket body, it does not fully exchange heat with the low temperature cold therapy liquid, and then flowing back into the cold therapy pad, resulting in poor cold therapy results.

It can be seen that in the prior art, the cold therapy equipment lacks temperature control, resulting in poor results of the cold therapy.

SUMMARY

In order to solve the above technical problems or at least partially solve the above technical problems, the present disclosure provides cold therapy systems and cold therapy devices that can more accurately control the temperature of the cold therapy fluid within the cold therapy pads.

In a first aspect, the present disclosure provides a cold therapy system, including a bucket body configured to store cold therapy fluid and a bucket lid;

The bucket lid includes: a first water circuit configured to input the cold therapy liquid from the bucket body to a cold therapy pad; a second water circuit configured to output the cold therapy liquid from the cold therapy pad to the bucket body; and a water pump configured to drive the cold therapy liquid to flow in a loop including the first water circuit, the second water circuit, and the bucket body.

The first water circuit includes: a pumping orifice, provided on a projecting portion of the bucket lid projecting into the bucket body, and immersed in the cold therapy liquid in the bucket body, the projecting portion including one or more pumping orifices; a first guide tube, a first end of the first guide tube being connected to the pumping orifice and the second end of the first guide tube being connected to an inlet port of the water pump; and a second guide tube, a first end of the second guide tube being connected to an outlet port of the water pump and a second end of the second guide tube being connected to an inlet pipe of the cold therapy pad.

The second water circuit includes: at least one return orifice with an opening facing in the direction of the bucket body, provided on a side of the bucket lid away from the projecting portion, and provided at a predetermined distance from the pumping orifice; and a third guide tube, a first end of the third guide tube being connected to an outlet pipe of the cold therapy pad and a second end of the third guide tube being connected to the return orifice.

In a second aspect, the present disclosure provides a cold therapy device including a cold therapy system as the first aspect, and a cold therapy pad connected to the cold therapy system and configured to fit a cold therapy area for cold therapy.

In an embodiment of the second aspect of the present disclosure, the cold therapy system includes a bucket body configured to store cold therapy fluid and a bucket lid; the bucket lid includes a first water circuit configured to input the cold therapy liquid from the bucket body to a cold therapy pad, a second water circuit configured to output the cold therapy liquid from the cold therapy pad to the bucket body, and a water pump configured to drive the cold therapy liquid to flow in a loop including the first water circuit, the second water circuit, and the bucket body. The first water circuit includes a pumping orifice, provided on a projecting portion of the bucket lid projecting into the bucket body, and immersed in the cold therapy liquid in the bucket body, the projecting portion comprises one or more pumping orifices, a first guide tube, a first end of the first guide tube being connected to the pumping orifice and the second end of the first guide tube being connected to an inlet port of the water pump; and a second guide tube, a first end of the second guide tube being connected to an outlet port of the water pump and a second end of the second guide tube being connected to an inlet pipe of the cold therapy pad. The second water circuit includes at least one return orifice with an opening facing in the direction of the bucket body, provided on a side of the bucket lid away from the projecting portion, and provided at a predetermined distance from the pumping orifice, and a third guide tube, a first end of the third guide tube being connected to an outlet pipe of the cold therapy pad and a second end of the third guide tube being connected to the return orifice. In this embodiment of the present disclosure, two water circuits are adopted. The first water circuit inputs the cold therapy liquid from the bucket body to the cold therapy pad, and the second water circuit outputs the cold therapy liquid from the cold therapy pad to the bucket body, which can separate the cold therapy liquid of a low temperature from the cold therapy liquid of a high temperature, and the setting of the pumping orifice and the return orifice can make the cold therapy liquid flowing from the return orifice to be fully mixed with the cold therapy liquid in the bucket body for heat exchange, avoiding the cold therapy liquid flowing from the return orifice directly into the pumping orifice and into the cold therapy pad, so as to better control the temperature of the cold therapy liquid entering the cold therapy pad and achieve a better cooling effect. Furthermore, only one water pump is adopted in this embodiment of the present disclosure to realize the flow of the cold therapy liquid, which can reduce the cost.

BRIEF DESCRIPTION OF THE DRAWINGS

The accompanying drawings herein, which are incorporated into and form a part of the specification, illustrate

DETAILED DESCRIPTION

In order to make the objects, technical solutions and advantages of the embodiments of the present disclosure clearer, the technical solutions in the embodiments of the present disclosure will be described clearly and completely in the following in conjunction with the accompanying drawings in the embodiments of the present disclosure, and it is clear that the described embodiments are part of the embodiments of the present disclosure, not all of the embodiments. Based on the embodiments in the present disclosure, all other embodiments obtained by a person of ordinary skill in the art without making creative labour fall within the scope of protection of the present disclosure. We list numbering of the components in the figures as below.

1: bucket body; 11: connecting lug; 2: bucket lid; 21: second stop plate; 22: projecting portion; 3: lifting handle; 31: limiting hole; 311: first end portion; 312: second end portion; 32: first protrusion; 33: holding portion; 4: knob; 41: first stop plate; 42: second protrusion; 120: first water circuit; 121: pumping orifice; 122: first guide tube; 123: second guide tube; 130: second water circuit; 131: return orifice; 132: third guide tube; 140: temperature detection circuit; 150: control circuit; 160: water pump; 161: drain tube; 170: pipeline detection circuit; 180: air guide tube; 190: air pump; 191: solenoid valve; 192: pressure relief valve; 201: output tube; 202: tube fitting; 203: cold therapy pad; 204: inlet pipe; 205: outlet pipe; 206: intake tube; 210: first controller; 220: first driver; 310: second controller; 320: second driver; 410: micro-controller (MCU); R1: thermistor; R2: second resistor; R3: third resistor; R4: fourth resistor; R5: fifth resistor; R6: sixth resistor; R7: seventh resistor; R8: eighth resistor; R9: ninth resistor; R10: tenth resistor; R11: eleventh resistor; R12: twelfth resistor; R13: thirteenth resistor; R14: fourteenth resistor; R15: fifteenth resistor; R16: sixteenth resistor; R17: seventeenth resistor; R18: eighteenth resistor; U1: first amplifier; U2: second amplifier; U3: third amplifier; C1: first capacitor; C2: second capacitor; D1: first diode; D2: second diode; Q1: first switch; Q2: second switch; REF: reference voltage terminal; VCC: first power supply.

Figure 1:
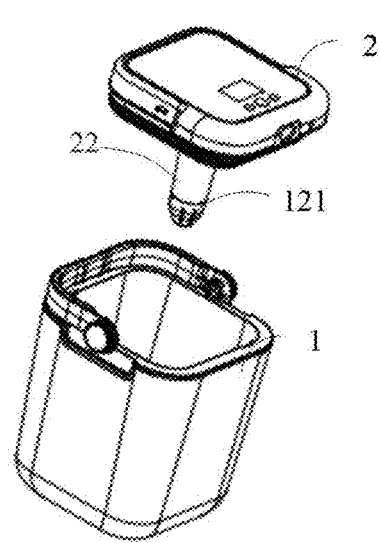
FIG. 1 is a schematic diagram of a cold therapy system of one or more embodiments of the present disclosure.
Figure 2:
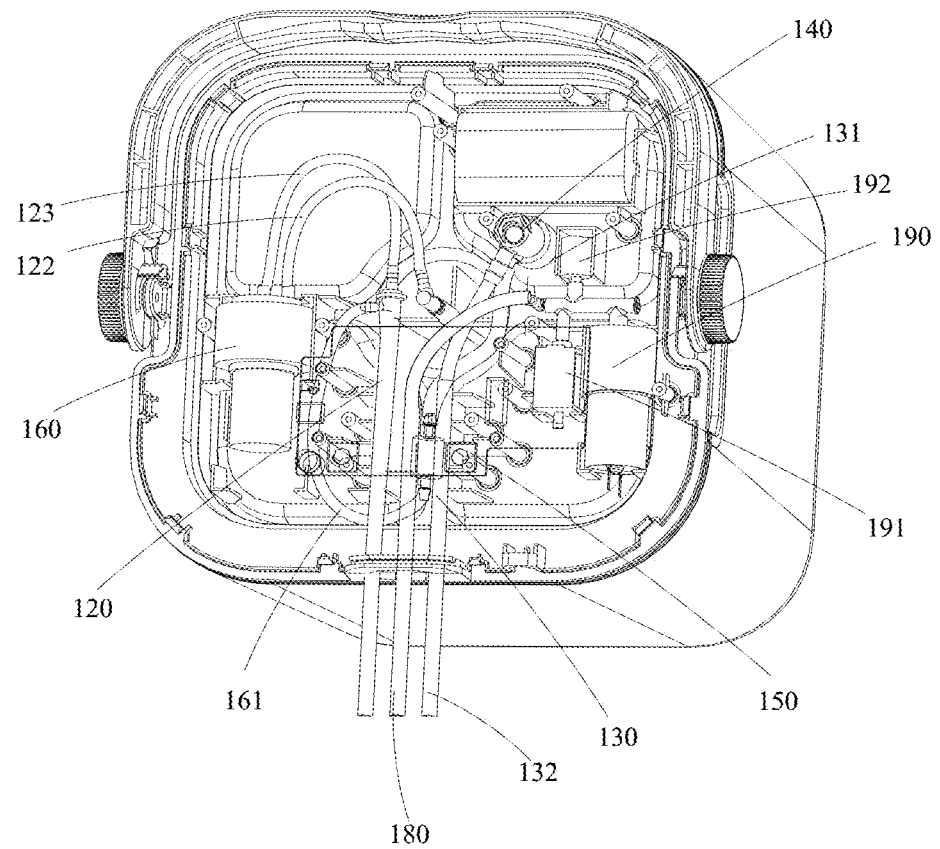
FIG. 2 is a schematic diagram of a cold therapy system of one or more embodiments of the present disclosure.

FIG. 1 and FIG. 2 illustrate schematic diagrams of a cold therapy system of one or more embodiments of the present disclosure, cold therapy system includes: a bucket body 1 configured to store cold therapy fluid; a first water circuit 120 configured to input the cold therapy liquid from the bucket body 1 to a cold therapy pad 203; a second water circuit 130 configured to output the cold therapy liquid from the cold therapy pad 203 to the bucket body 1; a temperature detection circuit 140, provided on the second water circuit 130, configured to detect a temperature of the cold therapy liquid output from the cold therapy pad 203 and output a temperature voltage; a control circuit 150 configured to generate a first control signal based on the temperature voltage; and a water pump 160 configured to drive the cold therapy liquid to flow in a loop formed by the first water circuit 120, the second water circuit 130, and the bucket body 1 according to the first control signal.

In an embodiment of the present disclosure, the cold therapy liquid may be an ice-water mixture, or may be an ice-salt-water mixture, or may be other liquids that can maintain a low temperature for a longer period of time. In an embodiment of the present disclosure, the cold therapy liquid may also be ordinary water, and the cold therapy system is provided with a cooling device, such as a compressor containing a refrigerant, or the like.

The bucket body 1 may be a bucket with a rectangular or square cross-section as shown in FIG. 1, or it may be a bucket with a circular cross-section, which will not be repeated here.

The first water circuit 120, the second water circuit 130, the temperature detection circuit 140, the control circuit 150, the water pump 160, and the like of the present disclosure may be provided on the bucket lid 2 above the bucket body 1 as shown in FIG. 2, or may be provided on the side (not shown on the drawings), or the bottom (not shown on the drawings) of the bucket body 1.

The cold therapy pad 203 fits the cold therapy site for cold therapy, the cold therapy liquid inside the cold therapy pad 203 exchanges heat with the cold therapy site, and the temperature of the cold therapy liquid will rise, wherein too high a temperature of the cold therapy liquid will result in poor cold therapy results. In the embodiment of the present disclosure, the temperature detection circuit 140 is disposed on the second water circuit 130, i.e., the temperature detection circuit 140 is disposed on the water circuit flowing from the cold therapy pad 203 to the bucket body 1, which is configured to more accurately detect the temperature of the cold therapy liquid flowing out of the cold therapy pad 203. And when the water pump 160 is turned off, according to the inertia, the cold therapy liquid will still continue to flow to the bucket body 1, which ensures that the cold therapy liquid is always in the flow state, to achieve dynamic temperature measurement of the temperature detection circuit 140, so that the temperature of the cold therapy liquid in the cold therapy pad 203 can be more accurately controlled, which helps to stabilize the cold therapy effect.

As shown in FIG. 2, the second water circuit 120 includes: a pumping orifice 121, immersed in the cold therapy liquid in the bucket body; a first guide tube 122, a first end of the first guide tube being connected to the pumping orifice 121 and the second end of the first guide tube being connected to an inlet port of the water pump; and a second guide tube 123, a first end of the second guide tube being connected to an outlet port of the water pump 160 and a second end of the second guide tube being connected to an inlet pipe 204 of the cold therapy pad 203.

The second water circuit 130 includes: at least one return orifice 131 with an opening facing in the direction of the bucket body 1, provided at a predetermined distance from the pumping orifice 121; and a third guide tube 132, a first end of the third guide tube being connected to an outlet pipe 205 of the cold therapy pad 203 and a second end of the third guide tube being connected to the return orifice 131.

In some embodiments, the bucket lid further comprises a temperature detection circuit, provided on the second water circuit, configured to detect a temperature of the cold therapy liquid output from the cold therapy pad 203 and output a temperature voltage; a control circuit configured to generate a first control signal based on the temperature voltage; the water pump configured to drive the cold therapy liquid to flow in a loop formed by the first water circuit, the second water circuit and the bucket body according to the first control signal.

In some embodiments, the temperature detection circuit includes: a temperature detector, provided within the third guide tube configured to detect the temperature of the cold therapy liquid within the third guide tube. The temperature detector includes: a thermistor, a first end of the thermistor being connected to the control circuit and a second end of the thermistor being grounded; and the resistance value of the thermistor decreases as the temperature of the cold therapy liquid detected increases.

In some embodiments, the control circuit includes: a first controller, connected to the temperature detection circuit, configured to generate the first control signal when the temperature of the cold therapy liquid detected by the temperature detection circuit is greater than or equal to a preset temperature; and a first driver, connected to the first controller, configured to generate a first switching signal according to the first control signal to turn on or turn off the water pump, so that the water pump, when turned on, drives the cold therapy liquid to flow in the loop formed by the first water circuit, the second water circuit and the bucket body.

In some embodiments, the first controller is further configured to generate the first control signal after a delay of a first preset duration when the temperature of the cold therapy liquid detected by the temperature detection circuit is greater than or equal to the preset temperature.

In some embodiments, the first controller includes: a first processor configured to generate a temperature control signal when the temperature of the cold therapy liquid detected by the temperature detection circuit is greater than or equal to a preset temperature, the temperature control signal being sent to the first time delayer; and a first time delayer configured to receive the temperature control signal and generate the first control signal based on the temperature control signal after the first preset duration.

In some embodiments, the first time delayer is further configured to receive a time delay command and set the first preset duration according to the time delay command.

In some embodiments, the first controller is further configured to generate the first control signal after a delay of a second preset duration when the water pump is switched off, so as to drive the water pump to be switched on again.

In some embodiments, the first controller includes: a second processor configured to generate a drive signal when the water pump is switched off and the drive signal is sent to the second time delayer; and a second time delayer configured to receive the drive signal and generate the first control signal based on the drive signal after the second preset duration.

In some embodiments, the second time delayer is further configured to receive a time delay command and set the second preset duration according to the time delay command.

In some embodiments, the cold therapy system further includes: a pipeline detection circuit, connected to the water pump, configured to detect a drive current of the water pump and output a pipeline voltage according to the drive current.

The control circuit further configured to generate a second control signal based on the pipeline voltage.

The water pump further configured to continue to drive the cold therapy liquid to flow or close in the loop formed by the first water circuit, the second water circuit and the bucket body according to the second control signal; wherein the drive current of the water pump is elevated in response to clogging of the line.

In some embodiments, wherein the control circuit further includes: a second controller, connected to the pipeline detection circuit, configured to generate the second control signal when the pipeline detection circuit detects that the current of the water pump is greater than or equal to a preset current; and a second driver, connected to the second controller, configured to generate a second switching signal according to the second control signal to continue to switch on or off the water pump, so that the water pump continues to be switched on when the pipeline is clear and switched off when the pipeline is clogged.

In some embodiments, the bucket lid is further provided with an air guide tube and an air pump, one end of the air guide tube being connected to the air pump, the other end of the air guide tube being connected to an intake tube 206 of the cold therapy pad 203, and the air pump inflating the cold therapy pad 203 through the air guide tube.

In some embodiments, the bucket lid further comprises a timer for setting the working time of the water pump.

In some embodiments, the cold therapy system further includes a lifting handle, the bucket lid closing on the bucket body, the ends of the lifting handle being rotationally connected to both sides of the bucket body respectively, and the lifting handle being provided with a locking structure configured to prevent the bucket lid from falling off.

The locking structure includes a first stop plate and a second stop plate, the second stop plate being disposed on a side wall of the bucket lid, the first stop plate being disposed on the lifting handle and the first stop plate being configured to rotate to stop on the top of the second stop plate so that the bucket lid is locked to the bucket body.

In some embodiments, the lifting handle is provided with a knob, the knob being rotatably attached to an end of the lifting handle, and the first stop plate is provided on the knob.

The knob is located on the outside of the lifting handle, the bucket lid is located on the inside of the lifting handle, the lifting handle is provided with a limiting hole, the first stop plate penetrates the limiting hole and is configured to rotate within the limiting hole.

In some embodiments, atop of the second stop plate is a curved structure, a bottom of the first stop plate is also a curved structure, and the limiting hole is a curved through-hole; and the locking structure is provided on both sides of the lifting handle, the bucket body is provided with connecting lugs on both sides, the connecting lugs, the lifting handle and the knob being coaxially rotationally connected.

In some embodiments, the limiting hole has a first end portion and a second end portion;

When the lifting handle is held upright on the bucket body and the first stop plate is pressed against the first end portion, the first stop plate stops at the top of the second stop plate, enabling the bucket lid to be locked to the bucket body; when the lifting handle is upright on the bucket body and the first stop plate is pressed against the second end portion, the first stop plate is away from the second stop plate, enabling the bucket lid to be unlocked to be opened.

When the lifting handle is closed over the bucket body and the first stop plate is pressed against the second end portion, the first stop plate stops at the top of the second stop plate, enabling the bucket lid to be locked to the bucket body; when the lifting handle is closed over the bucket body and the first stop plate is pressed against the first end portion, the first stop plate is away from the second stop plate, enabling the bucket lid to be unlocked to be opened.

In some embodiments, the limiting hole is provided with a first protrusion on the periphery of the limiting hole, and the first stop plate is provided with a second protrusion, the second protrusion being configured to cooperate with the first protrusion.

In some embodiments, the lifting handle is provided with a holding portion, and the holding portion is provided with a rubber sleeve.

In the embodiment of the present disclosure shown in FIG. 1, the first water circuit 120, the second water circuit 130 are provided on the bucket lid 2 above the bucket body 1, and the pumping orifice 121 is provided on a projecting portion 22 of the bucket lid 2 projecting into the bucket body 1. The projecting portion 22 may be an approximately cylindrical structure, and the return orifice 131 is provided on a side of the bucket lid 2 away from the projecting portion 22, such that the pumping orifice 121 and the return orifice 131 are spaced apart by a certain distance. As shown in FIG. 2, the return orifice 131 may be provided under the temperature detection circuit 140, with the opening facing the direction of the bucket body 1. The cold therapy liquid flowing from the return orifice 131 has a higher temperature, and being at a predetermined distance from the pumping orifice 121 allows the cold therapy liquid flowing from the return orifice 131 to be sufficiently mixed with the cold therapy liquid in the bucket body 1 for heat exchange, which avoids the cold therapy liquid flowing from the return orifice 131 from flowing back into the pumping orifice 121 and into the cold therapy pad 203.

Figure 5:
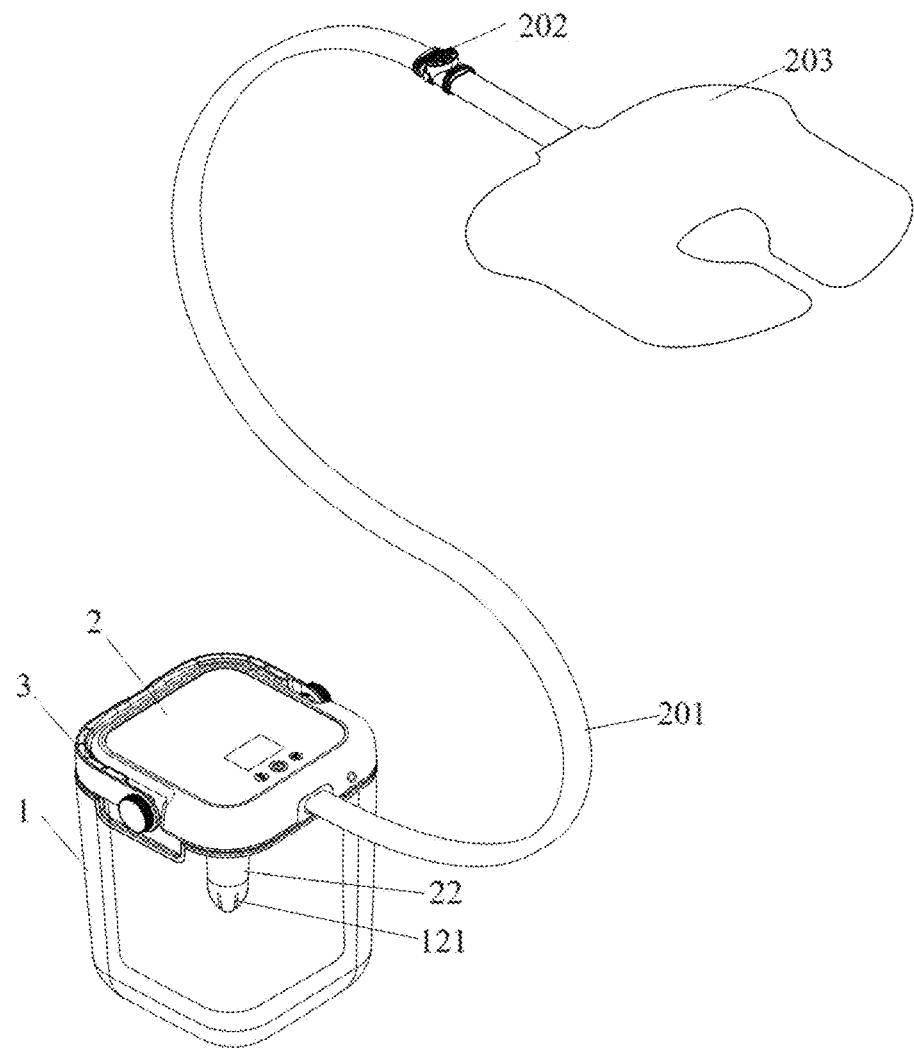
FIG. 5 is a schematic diagram of a cold therapy device of one or more embodiments of the present disclosure.
Figure 6:
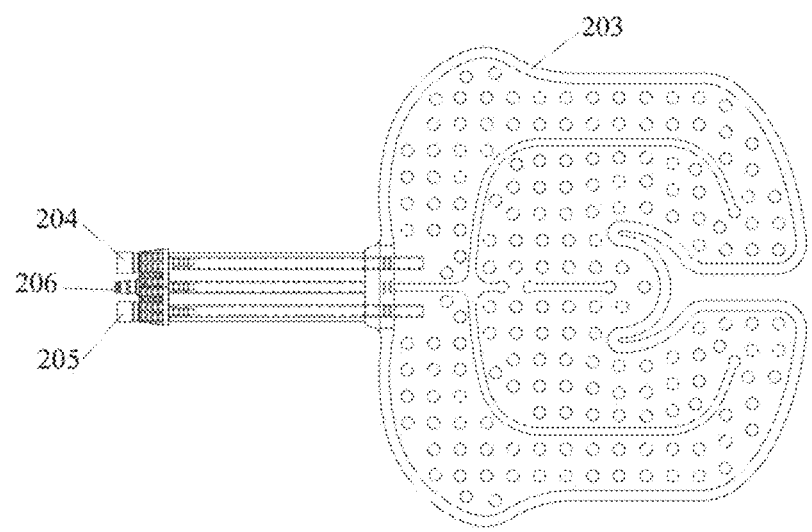
FIG. 6 is a schematic diagram of a cold therapy pad of one or more embodiments of the present disclosure.
Figure 7:
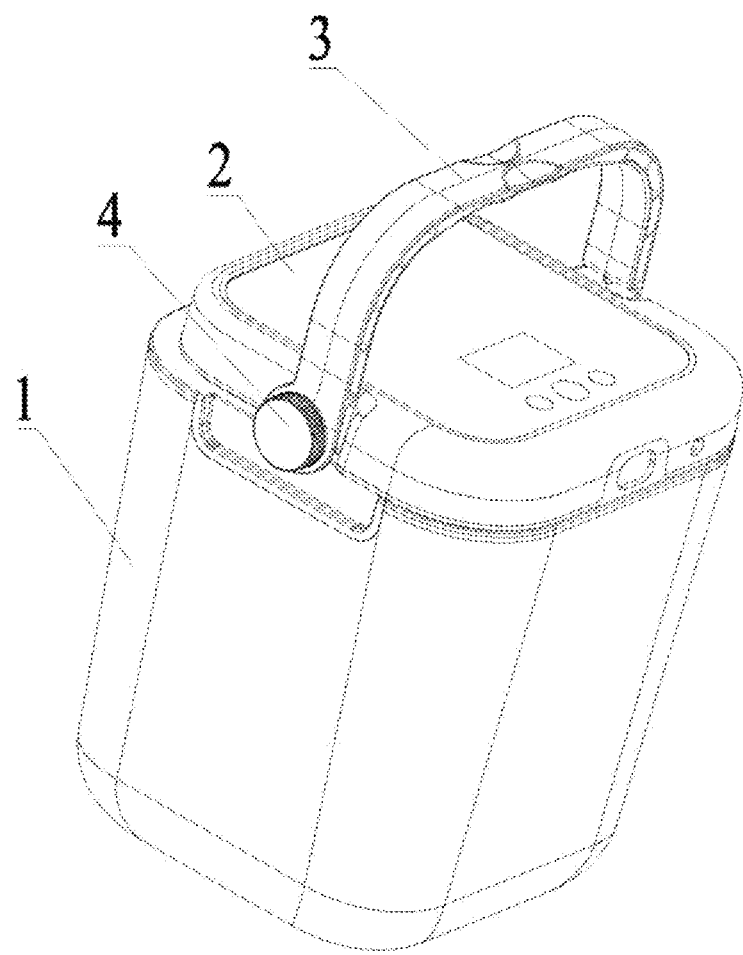
FIG. 7 is a schematic diagram of the structure of a cold therapy system of one or more embodiments of the present disclosure.
Figure 8:
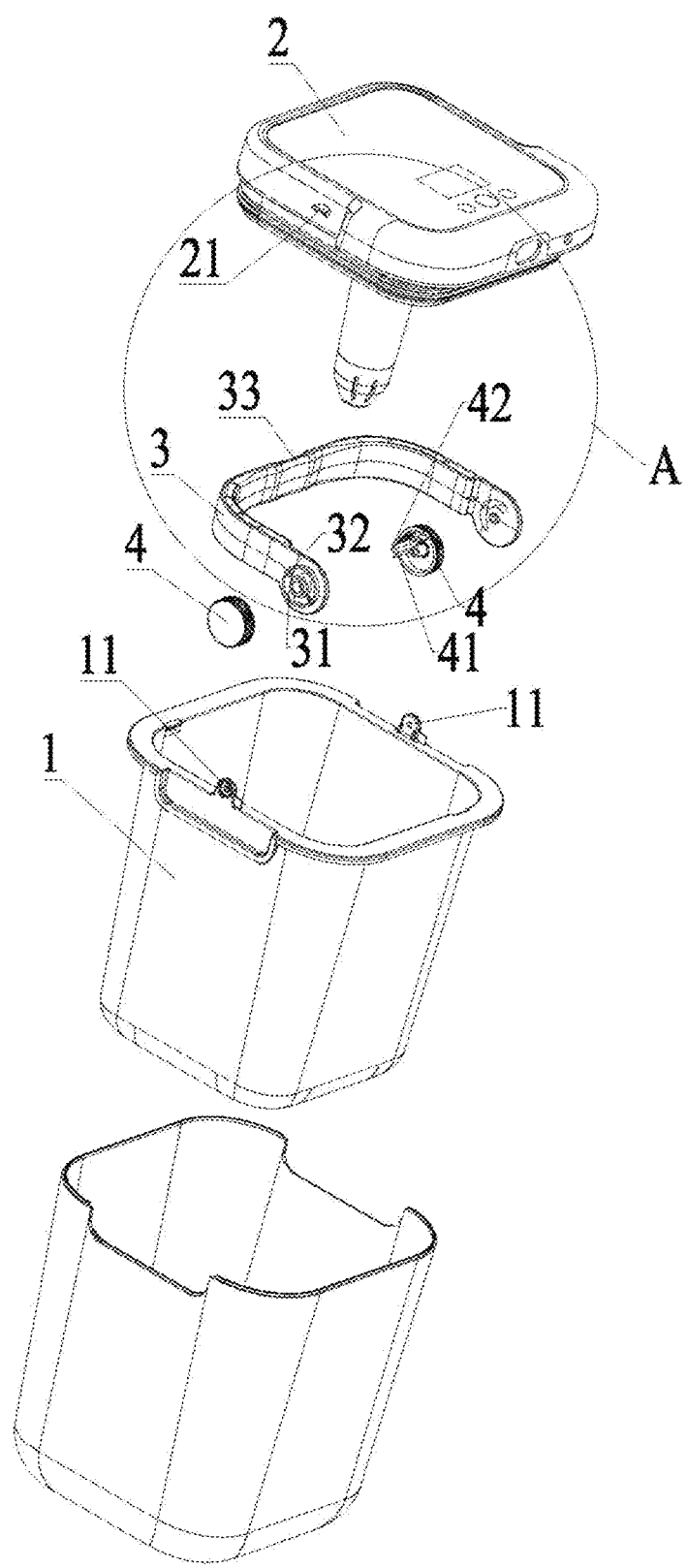
FIG. 8 is a decomposition diagram of a cold therapy system of one or more embodiments of the present disclosure.
Figure 9:
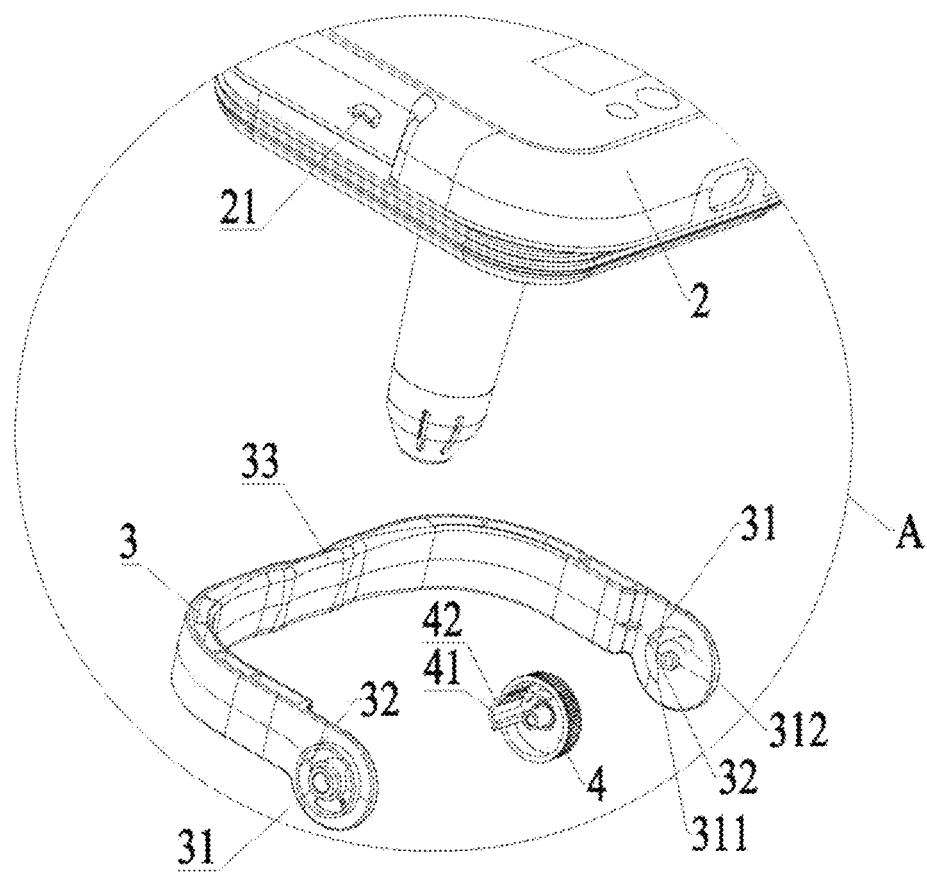
FIG. 9 is an enlarged view of portion A in FIG. 8.
Figure 10:
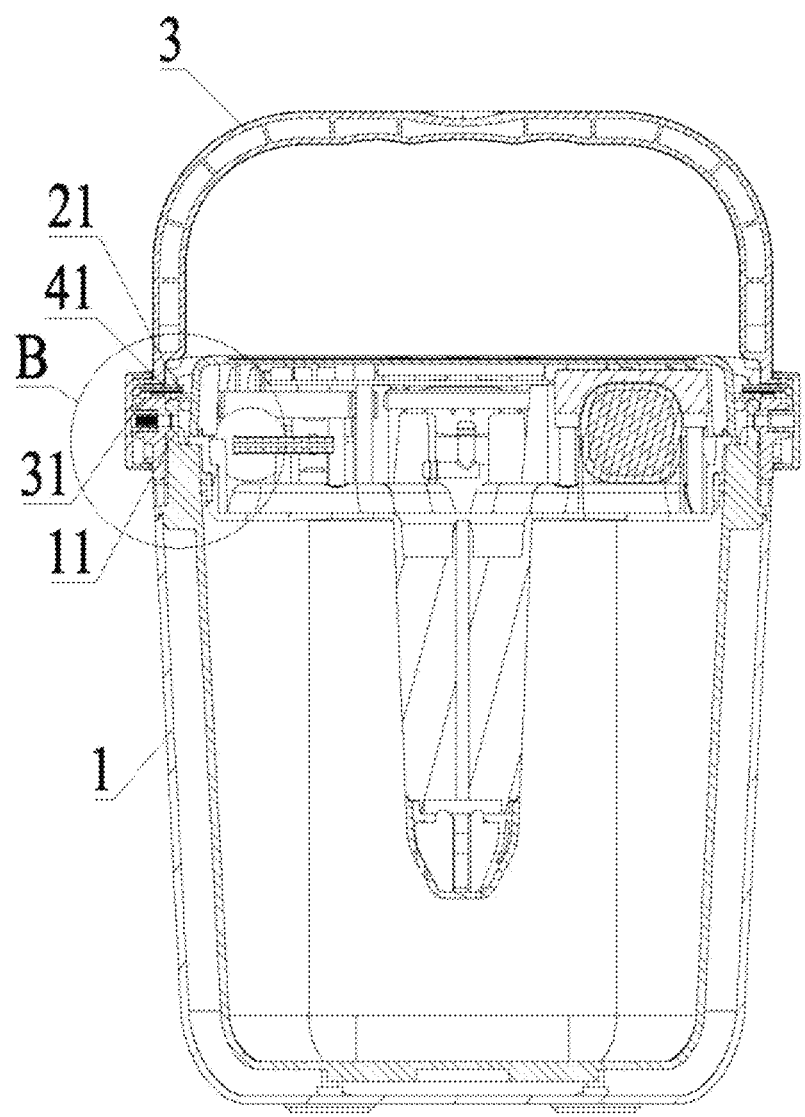
FIG. 10 is a side profile diagram of a cold therapy system of one or more embodiments of the present disclosure.
Figure 11:
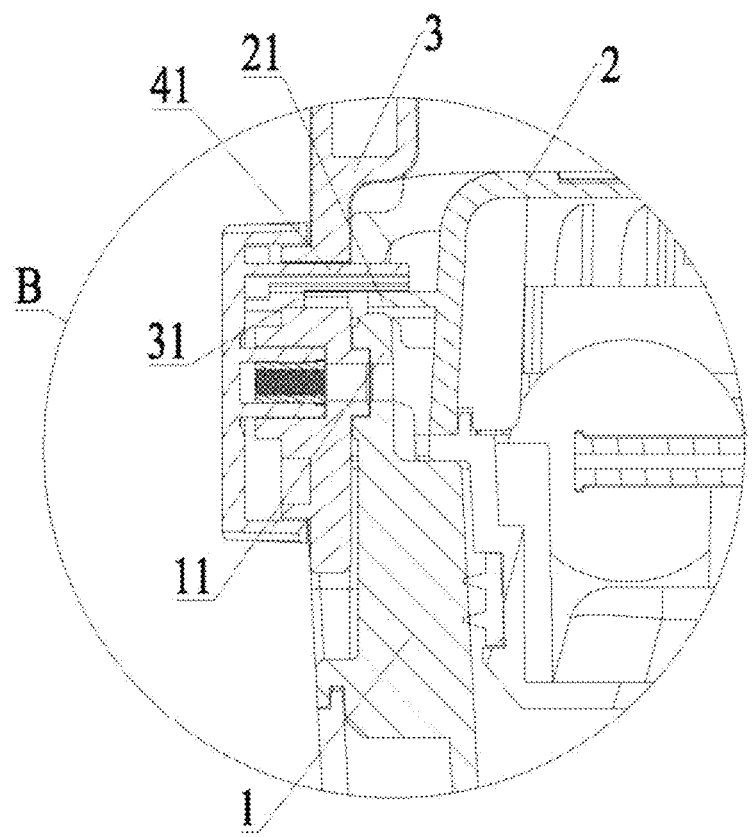
FIG. 11 is an enlarged view of portion B in FIG. 10.
Figure 12:
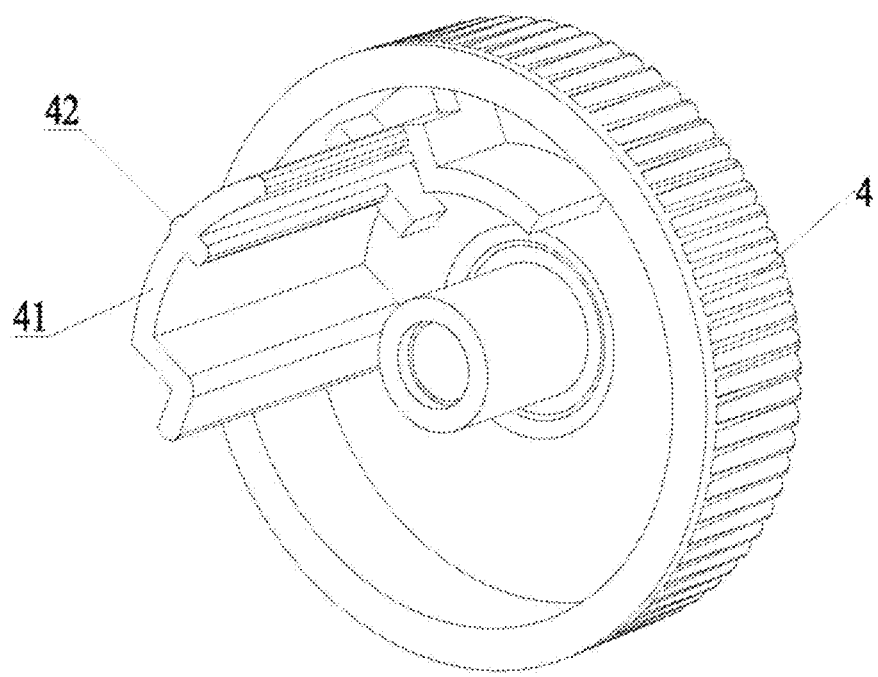
FIG. 12 is a schematic diagram of the structure of a knob of one or more embodiments of the present disclosure.

In one or more embodiments of the present disclosure, as shown in FIGS. 5-6, the cold therapy system further includes: an output tube 201.

The first end of the output tube 201 is fixedly or removably provided on the bucket lid 2, and the second end of output tube 201 extends out of the bucket lid 2 and is removably provided on the cold therapy pad 203 through a tube fitting 202. The output tube 201 has a first channel and a second channel formed through the ends of the output tube 201. The second guide tube 123 is connected to an inlet pipe 204 of the cold therapy pad 203 through the first channel and the third guide tube 132 is connected to outlet pipe 205 of the cold therapy pad 203 through the second channel.

The first end of the output tube 201 fixedly or removably provided on the bucket lid 2 above the bucket body 1 and the second end of output tube 201 extending out of the bucket lid 2 above the bucket body 1.

In this embodiment of the present disclosure, two water circuits are adopted. The first water circuit 120 inputs the cold therapy liquid from the bucket body 1 to the cold therapy pad 203, and the second water circuit 130 outputs the cold therapy liquid from the cold therapy pad 203 to the bucket body 1, which can separate the cold therapy liquid of a low temperature from the cold therapy liquid of a high temperature. Furthermore, only one water pump 160 is adopted in this embodiment of the present disclosure to realize the flow of the cold therapy liquid, which can reduce the cost. And by setting the temperature detection circuit 140 on the second water circuit 130, the temperature of the cold therapy liquid in the cold therapy pad 203 can be controlled more precisely.

Figure 3:
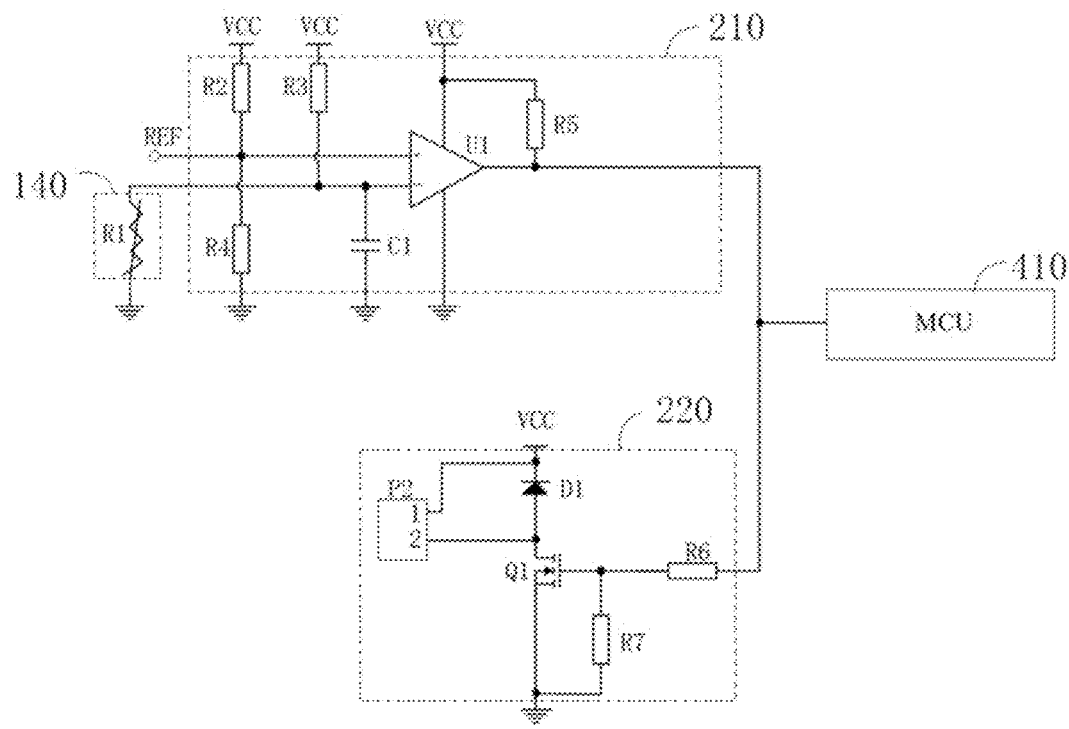
FIG. 3 is a schematic diagram of a temperature detection circuit and a control circuit of one or more embodiments of the present disclosure.

FIG. 3 is a schematic diagram of a temperature detection circuit and a control circuit of one or more embodiments of the present disclosure. In this embodiment of the present disclosure, the temperature detection circuit 140 includes: a temperature detector, provided within the third guide tube 132 configured to detect the temperature of the cold therapy liquid within the third guide tube 132.

In a embodiment of the present disclosure, the temperature detector includes a thermistor, a first end of the thermistor being connected to the control circuit and a second end of the thermistor being grounded.

The resistance value of the thermistor decreases as the temperature of the cold therapy liquid detected increases.

In a embodiment of the present disclosure, the control circuit 210 includes: a first controller 210, connected to the temperature detection circuit 140, configured to generate the first control signal when the temperature of the cold therapy liquid detected by the temperature detection circuit 140 is greater than or equal to a preset temperature; and a first driver 220, connected to the first controller 210, configured to generate a first switching signal according to the first control signal to turn on or turn off the water pump 160, so that the water pump 160, when turned on, drives the cold therapy liquid to flow in the loop formed by the first water circuit 120, the second water circuit 130 and the bucket body 1.

The control circuit 210 further includes: a first amplifier U1, the forward input of the first amplifier U1 is connected to a reference voltage terminal, the reverse input of the first amplifier U1 is connected to the temperature detection circuit 140, the power supply terminal of the first amplifier U1 is connected to a first power supply VCC, the output terminal of the first amplifier U1 is connected to the first driver 220, and the ground terminal of the first amplifier U1 is grounded; a second resistor R2, the first end of which is connected to the first power supply VCC and the second end of which is connected to the forward input of the first amplifier U1; a third resistor R3, the first end of which is connected to the first power supply VCC and the second end of which is connected to the reverse input of the first amplifier U1; a fourth resistor R4, the first end of which is connected to the forward input of the first amplifier U1 and the second end of which is grounded; a first capacitor C1, the first end connected to the reverse input of the first amplifier U1 and the second end grounded; a fifth resistor R5, the first end of which is connected to the first power supply VCC and the second end of which is connected to the output of the first amplifier U1.

In some embodiments of the present disclosure, the first driver 220 includes: a sixth resistor R6, the first end of which is connected to the first controller 210; a seventh resistor R7, the first end connected to the second end of the sixth resistor R6, the second end grounded; a first diode D1, the cathode of which is connected to the first power supply VCC, the cathode of which is also connected to the first end of the water pump 160; a first switch Q1, the gate of the first switch Q1 being connected to the second end of the sixth resistor R6, the drain of the first switch Q1 being connected to the anode of the first diode D1, the drain of the first switch Q1 being further connected to the second end of the water pump 160, and the source of the first switch Q1 being grounded.

In this embodiment of the present disclosure, as shown in FIG. 3, the temperature detector can be a thermistor R1 whose resistance decreases with increasing temperature.

In other embodiments of the present disclosure, the temperature detector may also be a temperature probe, etc., which will not be described herein.

In embodiments of the present disclosure, the cold therapy system further includes a micro-controller (MCU) 410 for receiving the first control signal from the first controller 210 and generating a first alarm signal.

According to the first alarm signal, the current temperature and the alarm signal can be displayed in the display panel, which is used to prompt the user that the current temperature of the cold therapy liquid is higher than the preset temperature value, and that the cold therapy liquid should be replaced or the treatment should be stopped, so as to avoid affecting the therapy effect.

After the cold therapy pad 203 is applied to the cold therapy site for a period of time, the temperature of the cold therapy site is higher than the temperature of the cold therapy liquid, so the heat of the cold therapy site is conducted into the cold therapy liquid of the cold therapy pad 203, and the temperature of the cold therapy liquid in the cold therapy pad 203 rises. The thermistor R1 is provided in the third guide tube 132, i.e., in the outlet pipe 205 of the cold therapy pad 203, the temperature of the thermistor R1 rises, the resistance value of the thermistor R1 becomes lower, and the voltage at the reverse input terminal of the first amplifier U1 is lower, as the temperature of the cold therapy liquid rises. Since the forward input of the first amplifier U1 is connected to a reference voltage, when the voltage at the reverse input terminal is lower than the reference voltage, the first amplifier U1 outputs a high level and the first switch Q1 opens. After the first switch Q1 is opened, the water pump 160 is turned on to drive the cold therapy liquid to flow in the loop formed by the first water circuit 120, the second water circuit 130, and the bucket body 1. Since the cold therapy liquid in the bucket body 1 is a lower temperature liquid such as an ice-water mixture, the cold therapy liquid from the bucket body 1 enters the cold therapy pad 203 and the temperature of the cold therapy pad 203 is reduced.

In one or more embodiments of the present disclosure, if the reverse input terminal voltage continues to be lower than the reference voltage for a certain period of time, the MCU 410 receives the first control signal and then generates a first alarm signal to prompt the user for a temperature alarm.

After the temperature of the cold therapy pad 203 is lowered, the temperature of the thermistor R1 is lowered, the resistance value of the thermistor R1 becomes high, and the voltage at the reverse input terminal of the first amplifier U1 becomes large. When the voltage at the reverse input terminal of the first amplifier U1 is greater than or equal to the reference voltage, the first amplifier U1 outputs a low level, and the first switch Q1 is closed. After the first switch Q1 is turned off, the water pump 160 is turned off, and the cold therapy liquid, according to inertia, will still continue to flow to the bucket body 1, which in turn can ensure that the cold therapy liquid is always in a flow state. Then it realizes the dynamic temperature measurement of the temperature detection circuit 140, so as to more accurately control the temperature of the cold therapy liquid in the cold therapy pad 203, and to keep the temperature in the cold therapy pad 203 at a constant low temperature.

In one or more embodiments of the present disclosure, the first controller 210 is further used to generate the first control signal after a delay of a first preset duration when the temperature of the cold therapy liquid detected by the temperature detection circuit 140 is greater than or equal to the preset temperature.

In one or more embodiments of the present disclosure, the first controller 210 includes a first processor and a first time delayer, the first processor configured to generate a temperature control signal when the temperature of the cold therapy liquid detected by the temperature detection circuit 140 is greater than or equal to a preset temperature, the temperature control signal being sent to the first time delayer;

the first time delayer configured to receive the temperature control signal and generate the first control signal based on the temperature control signal after the first preset duration.

In one or more embodiments of the present disclosure, the first time delayer is further used to receive a time delay command and to set the first preset duration according to the time delay command.

In an embodiment of the present disclosure, the first controller 210 is further used to generate the first control signal after a delay of a first preset duration when the detected temperature of the cold therapy fluid is greater than or equal to the preset temperature.

When the cold therapy pad 203 is used, the temperature of the cold therapy liquid inside the cold therapy pad 203 will rise, but the temperature detected by the temperature detection circuit 140 is only the temperature in the second water circuit 130 rather than the temperature in the cold therapy pad 203. When the detected temperature is lower than the predetermined temperature does not mean that the temperature of the cold therapy liquid inside the cold therapy pad 203 is lower than the predetermined temperature, so delaying the switching off or switching on of the water pump 160 allows the cold therapy liquid in the cold therapy pad 203 to fully flow out of the cold therapy pad 203, which can make the detected temperature more reflective of the actual temperature in the cold therapy pad 203 to ensure that the temperature of the cold therapy liquid in the cold therapy pad 203 reaches the desired temperature.

In one or more embodiments of the present disclosure, the first controller 120 is further configured to generate the first control signal after a delay of a second preset duration when the water pump 160 is switched off, so as to drive the water pump 160 to be switched on again.

In one or more embodiments of the present disclosure, the first controller 120 includes a second processor configured to generate a drive signal when the water pump 160 is switched off and the drive signal is sent to the second time delayer; and a second time delayer configured to receive the drive signal and generate the first control signal based on the drive signal after the second preset duration.

In one or more embodiments of the present disclosure, the second time delayer is further configured to receive a time delay command and set the second preset duration according to the time delay command.

In one or more embodiments of the present disclosure, the first controller 120 is further used to generate the first control signal after a delay of a second preset duration, so as to drive the water pump 160 to be switched on again.

After the water pump 160 is switched off for a certain period of time, the first controller 120 controls the water pump 160 to be switched on again, thereby being configured to ensure that the cold therapy liquid is always in a flowing state, so as to enable the temperature detection circuit 140 to dynamically measure the temperature of the cold therapy liquid inside the cold therapy pad 203, and to accurately detect and regulate the temperature of the cold therapy liquid inside the cold therapy pad 203.

Figure 4:
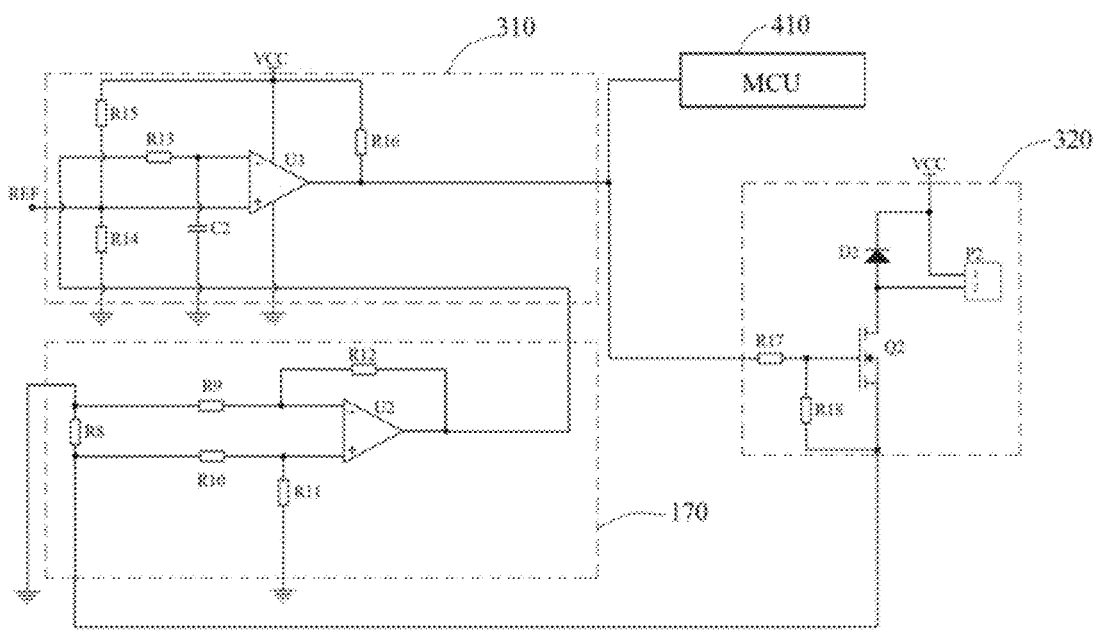
FIG. 4 is a schematic diagram of a pipeline detection circuit and a control circuit of one or more embodiments of the present disclosure.

FIG. 4 is a schematic diagram of a pipeline detection circuit and a control circuit of an embodiment of the present disclosure. In an embodiment of the present disclosure, the cold therapy system further includes: a pipeline detection circuit 170, connected to the water pump 160, configured to detect a drive current of the water pump 160 and output a pipeline voltage according to the drive current; the control circuit 150 further configured to generate a second control signal based on the pipeline voltage; and the water pump 160 further configured to continue to drive the cold therapy liquid to flow or close in the loop formed by the first water circuit 120, the second water circuit 130 and the bucket body 1 according to the second control signal; wherein the drive current of the water pump is elevated in response to clogging of the line.

The control circuit further includes: a second controller 310, connected to the pipeline detection circuit, configured to generate the second control signal when the pipeline detection circuit 170 detects that the current of the water pump 160 is greater than or equal to a preset current; and a second driver 320, connected to the second controller 310, configured to generate a second switching signal according to the second control signal to continue to switch on or off the water pump 160, so that the water pump 160 continues to be switched on when the pipeline is clear and switched off when the pipeline is clogged.

In an embodiment of the present disclosure, the pipe detection circuit 170 includes: a second amplifier U2, the output terminal of the second amplifier U2 being connected to the second controller 310; an eighth resistor R8 with a first end grounded and a second end connected to the second driver 320; a ninth resistor R9, the first end of which is grounded and the second end of which is connected to the reverse input of the second amplifier U2; a tenth resistor R10, the first end of which is connected to the second end of an eighth resistor R8, the second end of which is connected to the forward input of the second amplifier U2; an eleventh resistor R11, the first end connected to the forward input of the second amplifier U2 and the second end grounded; and a twelfth resistor R12, the first end connected to the reverse input terminal of the second amplifier U2 and the second end connected to the output terminal of the second amplifier U2.

In some embodiments of the present disclosure, the second controller 310 includes: a third amplifier U3, the forward input of the third amplifier U3 being connected to a reference voltage terminal, the power supply terminal of the third amplifier U3 being connected to a first power supply VCC, the output terminal of the third amplifier U3 being connected to the second driver, and the ground terminal of the third amplifier U3 being grounded; a thirteenth resistor R13, the first end of which is connected to the reverse input of the third amplifier U3, and the second end of which is connected to the pipeline detection circuit 170; a fourteenth resistor R14, the first end of which is connected to the forward input of the third amplifier U3, the second end of which is grounded; a fifteenth resistor R15, the first end of which is connected to the first power supply VCC and the second end of which is connected to the forward input of the third amplifier U3; a sixteenth resistor R16, the first end of which is connected to the first power supply VCC and the second end of which is connected to the output of the third amplifier U3; a second capacitor C2, the first end of which is connected to the reverse input of the third amplifier U3 and the second end of which is grounded.

In some embodiments of the present disclosure, the second driver 320 includes: a seventeenth resistor R17, the first end of which is connected to the second controller 310; an eighteenth resistor R18, the first end of which is connected to the second end of the seventeenth resistor R17, the second end being grounded; a second diode D2, the cathode of which is connected to the first power supply VCC, the cathode of which is also connected to the first end of the water pump 160; a second switch Q2, the gate of the second switch Q2 being connected to the second end of the seventeenth resistor R17, the drain of the second switch Q2 being connected to the anode of the second diode D2, the drain of the second switch Q2 being further connected to the second end of the water pump 160, and the source of the second switch Q2 being grounded.

In some embodiments of the present disclosure, the cold therapy system further includes:

the MCU 410 for receiving the second control signal from the second controller 310 and generating a second alarm signal to prompt the user in the display panel that the current pipeline is clogged and that the pipeline should be unclogged so as not to affect the treatment.

The pipeline detection circuit 170 is connected to the power supply of the water pump 160, and when the pipeline is free, the pipeline detection circuit 170 detects that the current of the water pump 160 is lower and the voltage at the reverse input terminal of the third amplifier U3 is lower. Since the forward input of the third amplifier U3 is connected to a reference voltage, when the voltage at the reverse input is less than or equal to the reference voltage, the third amplifier U3 outputs a high level and the second switch Q2 opens. After the second switch Q2 opens, the water pump 160 continues to turn on and continues to drive the cold therapy liquid to flow in the loop formed by the first water circuit 120, the second water circuit 130, and the bucket body 1.

When the pipeline is clogged, the pipeline detection circuit 170 detects that the current of the water pump 160 is elevated, and the voltage at the reverse input terminal of the third amplifier U3 is higher. Since the forward input of the third amplifier U3 is connected to a reference voltage, when the voltage at the reverse input is higher than the reference voltage, the third amplifier U3 outputs a low level, and the second switch Q2 is turned off. After the second switch Q2 is closed, the water pump 160 is turned off, and the MCU 410 receives the second control signal and generates a second alarm signal, which provides the user with a pipeline blockage alarm prompt, so that it can accurately detect whether or not the pipeline is clogged, and if it is clogged, it can turn off the water pump 160 in time.

In one or more embodiments of the present disclosure, the function of each resistor and capacitor may be a function such as filtering, isolation, voltage division, etc., so that the circuit can perform the above functions, and devices with the same or similar functions may be used instead, which will not be repeated herein.

As shown in FIG. 2, in one or more embodiments of the present disclosure, the bucket lid is further provided with an air guide tube 180 and an air pump 190, one end of the air guide tube 180 being connected to the air pump 190, the other end of the air guide tube 180 being connected to an intake tube 206 of the cold therapy pad 203, and the air pump 190 inflating the cold therapy pad 203 through the air guide tube 180. The output tube 201 also has a third channel formed through the ends of the output tube 201. The air guide tube 180 is connected to the intake tube 206 of the cold therapy pad 203 through the third channel.

In an embodiment of the present disclosure, the bucket lid 2 is further provided with a solenoid valve 191, the solenoid valve 191 is connected to the air guide tube 180 and used to deflating cold therapy pads 203.

In one or more embodiments of the present disclosure, the bucket lid 2 is further provided with a drain tube 161. One end of the drain tube 161 is connected to the inlet port of the water pump 160, and the other end of the drain tube 161 is connected to the return orifice 131 to allow for a balanced pressure inside and outside the cold therapy pad 203.

In one or more embodiments of the present disclosure, the bucket lid 2 is also provided with a pressure relief valve 192, the pressure relief valve 192 being connected to an air pump 190 and to a solenoid valve 191. the pressure relief valve 192 is used to open to deflate the cold therapy pad 203 when the air pressure inside the cold therapy pad 203 exceeds a preset pressure.

In one or more embodiments of the present disclosure, one end of the air conduit 180 is connected to the air pump 190, and the other end of the air conduit 180 is used to connect with the cold therapy pad 203, and the air pump 190 inflates the cold therapy pad 203 through the air guide tube 180, so that the cold therapy pad 203 is fitted to be pressed against the human body, so as to improve the cold therapy effect of the cold therapy liquid.

In one or more embodiments of the present disclosure, the solenoid valve 191 is connected to the air guide tube 180, and opening the solenoid valve 191 can deflate the cold therapy pad 203. The combination of inflating by the air pump 190 and deflating by the solenoid valve 191 enables the cold therapy pad 203 to have a medical effect such as massage.

In one or more embodiments of the present disclosure, when the air pump 190 is working, the solenoid valve 191 is off, and the cold therapy pad 203 is inflated through the air pump 190; when it needs to be deflated, the air pump 190 is off and the solenoid valve 191 is on, and the cold therapy pad 203 is deflated through the solenoid valve 191.

In one or more embodiments of the present disclosure, when one of the air pump 190 and the solenoid valve 191 is out of control or malfunctioning, or when the air pressure inside the cold therapy pad 203 is too high, the air is deflated through the pressure relief valve 192.

As shown in FIGS. 7-12, the present disclosure provides a cold therapy system, includes the bucket body 1, the bucket lid 2 and a lifting handle 3. The bucket lid 2 is closed on the bucket body 1, the ends of the lifting handle 3 are rotationally connected to both sides of the bucket body 1 respectively, and the lifting handle 3 is provided with a locking structure configured to prevent the bucket lid 2 from falling off. By providing a locking structure on the lifting handle 3, the bucket lid 2 is fixed to the bucket body 1 to avoid that the bucket lid 2 falls off from the bucket body 1 when the cold therapy system is knocked over or when the cold therapy system is lifted, resulting in overflow of cold therapy liquid in the bucket body 1, which is not easy to be cleaned up, and it is possible to avoid that the bucket lid 2 falls down and results in the damage of the component in the bucket lid 2.

In one or more embodiments of the present disclosure, the locking structure includes knob 4 and a second stop plate 21. The second stop plate 21 is disposed on a side wall of the bucket lid, the knob is rotatably attached to a end of the lifting handle, and a first stop plate is provided on the knob 41. The first stop plate 41 is able to rotate to stop on the top of the second stop plate so that the bucket lid is locked to the bucket body. Turning the knob 4 causes the first stop plate 41 to rotate to the top of the second stop plate 21, causing the locking of the bucket lid 2, and the knob 4 is provided with non-slip patterns on the outer periphery of the knob 4, which is convenient for rotational operation, and is able to quickly lock the bucket lid 2. When it needs to be unlocked, reversing the twisting of the knob 4 can cause the bucket lid 2 to be unlocked, and at this time the bucket lid 2 can be opened.

In one or more embodiments of the present disclosure, the knob 4 is located on the outside of the lifting handle 3, and the bucket lid 2 is located on the inside of the lifting handle 3. The lifting handle 3 is provided with a limiting hole 31, the first stop plate 41 penetrates the limiting hole 31 and is configured to rotate within the limiting hole 31. the limiting hole 31 is configured to limit the angle of rotation of the first stop plate 41 such that rotation of the knob 4 back and forth is configured to control the locking and unlocking of the bucket lid 2.

In one or more embodiments of the present disclosure, a top of the second stop plate 21 is a curved structure, a bottom of the first stop plate 41 is also a curved structure, and the limiting hole 31 is a curved through-hole. The arc length of the first stop plate 41 is less than that of the limiting hole 31 such that the first stop plate 41 is able to rotate in the limiting hole 31 and is able to rotate to the top of the second stop plate 21.

In one or more embodiments of the present disclosure, the limiting hole 31 has a first end portion 311 and a second end portion 312; when the lifting handle 3 is held upright on the bucket body 1 and the first stop plate 41 is pressed against the first end portion 311, the first stop plate 41 stops at the top of the second stop plate 21, enabling the bucket lid 2 to be locked to the bucket body 1; when the lifting handle 3 is upright on the bucket body 1 and the first stop plate 41 is pressed against the second end portion 312, the first stop plate 41 is away from the second stop plate 21, enabling the bucket lid 2 to be unlocked to be opened; when the lifting handle 3 is closed over the bucket body 1 and the first stop plate 41 is pressed against the second end portion 312, the first stop plate 41 stops at the top of the second stop plate 21, enabling the bucket lid 2 to be locked to the bucket body 1; and when the lifting handle 3 is closed over the bucket body and the first stop plate 41 is pressed against the first end portion 311, the first stop plate 41 is away from the second stop plate 21, enabling the bucket lid 2 to be unlocked to be opened.

In one or more embodiments of the present disclosure, the limiting hole 31 is provided with a first protrusion 32 on the periphery of the limiting hole 31, and the first stop plate 41 is provided with a second protrusion 42, the second protrusion 42 being configured to cooperate with the first protrusion 32. when the first stop plate 41 resists the first end portion 311, the second protrusion 42 resists the first protrusion 32 on a side away from the first end portion 311. At this time, lifting up the lifting handles 3, the lifting handles 3 rotates relative to the bucket lid 2, and the first end portion 311 drives the first stop plate 41 on the knob 4 to rotate to the top of the second stop plate 21. So the knob 4 locks the bucket lid 2 to prevent it from falling off, so as to realize lifting the lifting handle 3 and fixing the bucket lid 2 at the same time. When the lifting handle 3 is put down, the lifting handle 3 rotates relative to the bucket lid 2, and the first protrusion 32 drives the second protrusion 42 to rotate so as to make the first stop plate 41 to rotate along with the lifting handle 3 to a side far away from the second stop plate 21, then bucket lid 2 is unlock while 1 the lifting handle 3 is put down.

In the embodiment of the present disclosure, the locking structure is provided on both sides of the lifting handle 3, and two locking structures are provided on both sides of the lifting handle 3, and the left and right sides simultaneously fix the bucket lid 2, which is able to achieve a better fixing effect.

In an embodiment of the present disclosure, the bucket body 1 is provided with connecting lugs 11 on both sides. The connecting lugs 11, the lifting handle 3 and the knob 4 are coaxially rotationally connected. the lifting handle 3 is configured to rotate the knob 4 together when rotated relative to the connecting lug 11, so that the first stop plate 41 on the knob 4 can be rotated to the top of the second stop plate 21 to lock the bucket lid 2 from falling off. The knob 4 can be rotated individually to control the locking and unlocking of the bucket lid 2, or it can be rotated synchronously with the lifting handle 3 to control the locking and unlocking of the bucket lid 2.

In an embodiment of the present disclosure, the lifting handle 3 is provided with a holding portion 33, and the holding portion 33 is provided with a rubber sleeve. the rubber sleeve may be made of a soft rubber material, such as a silicone material or a rubber material, or it may be made of a hard rubber material, the rubber sleeve being configured to provide a layer of protection to the lifting handle 3, preventing the user from being cut by the lifting handle 3 when lifting the lifting handle 3.

When the lifting handle 3 is lifted, the lifting handle 3 drives the knob 4 to rotate together, so that the lifting handle 3 is lifted to the middle and at the same time is able to drive the first retainer 41 together to the top of the second stop plate 21, so as to lock the bucket lid 2. When the lifting handle 3 is put down and the second protrusion 42 of the first stop plate 41 is cooperating with the first protrusion 32, in this case, if it is needed to lock the bucket lid 2 alone without lifting the lifting handle 3, it is sufficient to apply an external force to the knob 4 to disengage the second protrusion 42 from the first protrusion 32, so that the knob 4 can be turned alone to lock the lid 2.

As shown in FIGS. 5-6, the present disclosure also discloses a cold therapy device including a cold therapy system as described above, further includes: a cold therapy pad 203, connected to the cold therapy system, for fitting the cold therapy site for cold therapy.

Embodiments of the present disclosure provide a cold therapy system and a cold therapy device. The cold therapy system includes: bucket body 1 configured to store cold therapy fluid; a first water circuit 120 configured to input the cold therapy liquid from the bucket body 1 to a cold therapy pad 203; a second water circuit 130 configured to output the cold therapy liquid from the cold therapy pad 203 to the bucket body 1; and a water pump 160 configured to drive the cold therapy liquid to flow in a loop formed by the first water circuit, the second water circuit and the bucket body. The first water circuit 120 includes a pumping orifice 121, provided on a projecting portion 22 of the bucket lid 2 projecting into the bucket body 1, and immersed in the cold therapy liquid in the bucket body 1, the projecting portion 22 including one or more pumping orifices 121, a first guide tube 122, a first end of the first guide tube 122 being connected to the pumping orifice 121 and the second end of the first guide tube 122 being connected to an inlet port of the water pump 160; and a second guide tube 123, a first end of the second guide tube 123 being connected to an outlet port of the water pump 160 and a second end of the second guide 123 tube being connected to an inlet pipe 204 of the cold therapy pad 203. The second water circuit 130 includes at least one return orifice 131 with an opening facing in the direction of the bucket body 1, provided on a side of the bucket lid 2 away from the projecting portion 22, and provided at a predetermined distance from the pumping orifice 121, and a third guide tube 132, a first end of the third guide tube 132 being connected to an outlet pipe 205 of the cold therapy pad 203 and a second end of the third guide tube 132 being connected to the return orifice 131. In this embodiment of the present disclosure, two water circuits are adopted. The first water circuit 120 inputs the cold therapy liquid from the bucket body 1 to the cold therapy pad 203, and the second water circuit 130 outputs the cold therapy liquid from the cold therapy pad 203 to the bucket body 1, which can separate the cold therapy liquid of a low temperature from the cold therapy liquid of a high temperature, and the setting of the pumping orifice 121 and the return orifice 131 can make the cold therapy liquid flowing from the return orifice 131 to be fully mixed with the cold therapy liquid in the bucket body 1 for heat exchange, avoiding the cold therapy liquid flowing from the return orifice 131 directly into the pumping orifice 121 and into the cold therapy pad 203, so as to better control the temperature of the cold therapy liquid entering the cold therapy pad 203 and achieve a better cooling effect. Furthermore, only one water pump 160 is adopted in this embodiment of the present disclosure to realize the flow of the cold therapy liquid, which can reduce the cost.

It should be noted that, in this document, relational terms such as "first" and "second" are used only to distinguish one entity or operation from another and do not necessarily require or imply the existence of any such actual relationship or order between those entities or operations. does not necessarily require or imply the existence of any such actual relationship or order between those entities or operations. Furthermore, the terms "including," "comprising," or any other variant thereof, are intended to cover non-exclusive inclusion, such that a process, method, article, or apparatus comprising a set of elements includes not only those elements but also other elements not expressly listed, or other elements that are not expressly listed for the purpose of such a process, method, article or apparatus, or other elements that are not expressly listed for the purpose of such a process, method, article or equipment. elements, or also includes elements that are inherent to such process, method, article or apparatus. Without further limitation, the fact that an element is defined by the phrase "includes a . . . " does not preclude the existence of additional identical elements in the process, method, article or apparatus that includes the element.

The foregoing are only specific embodiments of the present disclosure to enable those skilled in the art to understand or realize the disclosure. Various modifications to these embodiments will be apparent to those skilled in the art, and the general principles defined herein may be implemented in other embodiments without departing from the spirit or scope of the present disclosure. Accordingly, the present disclosure will not be limited to these embodiments shown herein, but will be subject to the broadest scope consistent with the principles and novel features invented herein.

What is claimed is:

1. A cold therapy system, comprising a bucket body configured to store cold therapy fluid and a bucket lid, wherein the bucket lid comprises:
   a first water circuit configured to input the cold therapy liquid from the bucket body to a cold therapy pad;
   a second water circuit configured to output the cold therapy liquid from the cold therapy pad to the bucket body; and
   a water pump configured to drive the cold therapy liquid to flow in a loop including the first water circuit, the second water circuit, and the bucket body;
   wherein the first water circuit comprises:
      one or more pumping orifices, provided on a projecting portion of the bucket lid projecting into the bucket body, and immersed in the cold therapy liquid in the bucket body;
      a first guide tube, a first end of the first guide tube being connected to the pumping orifice and a second end of the first guide tube being connected to an inlet port of the water pump; and
      a second guide tube, a first end of the second guide tube being connected to an outlet port of the water pump and a second end of the second guide tube being connected to an inlet pipe of the cold therapy pad; and
   wherein the second water circuit comprises:
      at least one return orifice with an opening facing in a direction of the bucket body, provided on a side of the bucket lid away from the projecting portion, and provided at a predetermined distance from the pumping orifice; and
      a third guide tube, a first end of the third guide tube being connected to an outlet pipe of the cold therapy pad and a second end of the third guide tube being connected to the at least one return orifice;
   wherein:
      the cold therapy system further comprises a lifting handle, the bucket lid closing on the bucket body, the ends of the lifting handle being rotationally connected to both sides of the bucket body respectively, and the lifting handle being provided with a locking structure configured to prevent the bucket lid from falling off;
      the locking structure comprises a first stop plate and a second stop plate, the second stop plate being disposed on a side wall of the bucket lid, the first stop plate being disposed on the lifting handle and the first stop plate being configured to rotate to stop on a top of the second stop plate so that the bucket lid is locked to the bucket body;
      the lifting handle is provided with a knob, the knob being rotatably attached to an end of the lifting handle, and the first stop plate is provided on the knob; and
      the knob is located on the outside of the lifting handle, the bucket lid is located on the inside of the lifting handle, the lifting handle is provided with a limiting hole, the first stop plate penetrates the limiting hole and is configured to rotate within the limiting hole.

2. The cold therapy system according to claim 1, wherein the bucket lid further comprises:
   a temperature detection circuit, provided on the second water circuit, configured to detect a temperature of the cold therapy liquid output from the cold therapy pad and output a temperature voltage; and
   a control circuit configured to generate a first control signal based on the temperature voltage; and
   wherein the water pump is configured to drive the cold therapy liquid to flow in the loop according to the first control signal.

3. The cold therapy system according to claim 2, wherein the temperature detection circuit comprises:
   a temperature detector, provided within the third guide tube configured to detect the temperature of the cold therapy liquid within the third guide tube;
   wherein:
      the temperature detector comprises a thermistor, a first end of the thermistor being connected to the control circuit and a second end of the thermistor being grounded, and a resistance value of the thermistor decreases as the temperature of the cold therapy liquid detected increases.

4. The cold therapy system according to claim 2, wherein the control circuit comprises:
   a first controller, connected to the temperature detection circuit, and configured to generate the first control signal when the temperature of the cold therapy liquid detected by the temperature detection circuit is greater than or equal to a preset temperature; and
   a first driver, connected to the first controller, and configured to generate a first switching signal according to the first control signal to turn on or turn off the water pump, so that the water pump, when turned on, drives the cold therapy liquid to flow in the loop including the first water circuit, the second water circuit, and the bucket body.

5. The cold therapy system according to claim 4, wherein the first controller is further configured to generate the first control signal after a delay of a first preset duration when the temperature of the cold therapy liquid detected by the temperature detection circuit is greater than or equal to the preset temperature.

6. The cold therapy system according to claim 5, wherein the first controller comprising:
   a first processor configured to generate a temperature control signal when the temperature of the cold therapy liquid detected by the temperature detection circuit is greater than or equal to a preset temperature, the temperature control signal being sent to a first time delayer; and
   the first time delayer configured to receive the temperature control signal and generate the first control signal based on the temperature control signal after the first preset duration.

7. The cold therapy system according to claim 6, wherein the first time delayer is further configured to receive a time delay command and set the first preset duration according to the time delay command.

8. The cold therapy system according to claim 4, wherein the first controller is further configured to generate the first control signal after a delay of a second preset duration when the water pump is switched off, so as to drive the water pump to be switched on again.

9. The cold therapy system according to claim 8, wherein the first controller comprising:
   a second processor configured to generate a drive signal when the water pump is switched off and the drive signal is sent to a second time delayer; and the second time delayer configured to receive the drive signal and generate the first control signal based on the drive signal after the second preset duration.

10. The cold therapy system according to claim 9, wherein the second time delayer is further configured to receive a time delay command and set the second preset duration according to the time delay command.

11. The cold therapy system according to claim 2, wherein the cold therapy system further comprises:
a pipeline detection circuit, connected to the water pump, configured to detect a drive current of the water pump and output a pipeline voltage according to the drive current;
wherein the control circuit is further configured to generate a second control signal based on the pipeline voltage;
wherein the water pump is further configured to continue to drive the cold therapy liquid to flow or close in the loop according to the second control signal; and
wherein the drive current of the water pump is elevated in response to clogging of the line.

12. The cold therapy system according to claim 11, wherein the control circuit further comprises:
a second controller, connected to the pipeline detection circuit, and configured to generate the second control signal when the pipeline detection circuit detects that the current of the water pump is greater than or equal to a preset current; and
a second driver, connected to the second controller, and configured to generate a second switching signal according to the second control signal to continue to switch on or off the water pump, so that the water pump continues to be switched on when the pipeline is clear and switched off when the pipeline is clogged.

13. The cold therapy system according to claim 1, wherein the bucket lid is further provided with an air guide tube and an air pump, one end of the air guide tube being connected to the air pump, the other end of the air guide tube being connected to an intake tube of the cold therapy pad, and the air pump inflating the cold therapy pad through the air guide tube.

14. The cold therapy system according to claim 1, wherein the bucket lid further comprises a timer for setting the working time of the water pump.

15. The cold therapy system according to claim 1, wherein the top of the second stop plate is a curved structure, a bottom of the first stop plate is also a curved structure, and the limiting hole is a curved through-hole; the locking structure is provided on both sides of the lifting handle, and the bucket body is provided with connecting lugs on both sides, the connecting lugs, the lifting handle and the knob being coaxially rotationally connected.

16. The cold therapy system according to claim 15, wherein:
the limiting hole has a first end portion and a second end portion;
when the lifting handle is held upright on the bucket body and the first stop plate is pressed against the first end portion, the first stop plate stops at the top of the second stop plate, enabling the bucket lid to be locked to the bucket body; when the lifting handle is upright on the bucket body and the first stop plate is pressed against the second end portion, the first stop plate is away from the second stop plate, enabling the bucket lid to be unlocked to be opened; and
when the lifting handle is closed over the bucket body and the first stop plate is pressed against the second end portion, the first stop plate stops at the top of the second stop plate, enabling the bucket lid to be locked to the bucket body; when the lifting handle is closed over the bucket body and the first stop plate is pressed against the first end portion, the first stop plate is away from the second stop plate, enabling the bucket lid to be unlocked to be opened.

17. The cold therapy system according to claim 16, wherein the limiting hole is provided with a first protrusion on a periphery of the limiting hole, and the first stop plate is provided with a second protrusion, the second protrusion being configured to cooperate with the first protrusion.

18. A cold therapy device comprising a cold therapy system and a cold therapy pad connected to the cold therapy system and configured to fit a cold therapy area for cold therapy,
wherein the cold therapy system comprises a bucket body configured to store cold therapy fluid and a bucket lid, wherein the bucket lid comprises:
a first water circuit configured to input the cold therapy liquid from the bucket body to a cold therapy pad;
a second water circuit configured to output the cold therapy liquid from the cold therapy pad to the bucket body; and
a water pump configured to drive the cold therapy liquid to flow in a loop including the first water circuit, the second water circuit, and the bucket body;
wherein the first water circuit comprises:
one or more pumping orifices, provided on a projecting portion of the bucket lid projecting into the bucket body, and immersed in the cold therapy liquid in the bucket body;
a first guide tube, a first end of the first guide tube being connected to the pumping orifice and a second end of the first guide tube being connected to an inlet port of the water pump; and
a second guide tube, a first end of the second guide tube being connected to an outlet port of the water pump and a second end of the second guide tube being connected to an inlet pipe of the cold therapy pad; and
wherein the first water circuit comprises:
at least one return orifice with an opening facing in a direction of the bucket body, provided on a side of the bucket lid away from the projecting portion, and provided at a predetermined distance from the pumping orifice; and
a third guide tube, a first end of the third guide tube being connected to an outlet pipe of the cold therapy pad and a second end of the third guide tube being connected to the at least one return orifice;
wherein:
the cold therapy system further comprises a lifting handle, the bucket lid closing on the bucket body, the ends of the lifting handle being rotationally connected to both sides of the bucket body respectively, and the lifting handle being provided with a locking structure configured to prevent the bucket lid from falling off;
the locking structure comprises a first stop plate and a second stop plate, the second stop plate being disposed on a side wall of the bucket lid, the first stop plate being disposed on the lifting handle and the first stop plate being configured to rotate to stop on a top of the second stop plate so that the bucket lid is locked to the bucket body;

the lifting handle is provided with a knob, the knob being rotatably attached to an end of the lifting handle, and the first stop plate is provided on the knob; and the knob is located on the outside of the lifting handle, the bucket lid is located on the inside of the lifting handle, the lifting handle is provided with a limiting hole, the first stop plate penetrates the limiting hole and is configured to rotate within the limiting hole.

* * * * *